(12) United States Patent
Fuerstenberg et al.

(10) Patent No.: US 10,575,922 B2
(45) Date of Patent: Mar. 3, 2020

(54) X-RAY SYSTEM COMPRISING AN X-RAY SOURCE

(71) Applicant: Siemens Healthcare GmbH, Erlangen (DE)

(72) Inventors: Dieter Fuerstenberg, Erlangen (DE); Klaus Steiger, Uttenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 101 days.

(21) Appl. No.: 15/749,600

(22) PCT Filed: Aug. 1, 2016

(86) PCT No.: PCT/EP2016/068298
§ 371 (c)(1),
(2) Date: Feb. 1, 2018

(87) PCT Pub. No.: WO2017/025369
PCT Pub. Date: Feb. 16, 2017

(65) Prior Publication Data
US 2018/0214244 A1 Aug. 2, 2018

(30) Foreign Application Priority Data

Aug. 12, 2015 (DE) .......... 10 2015 215 377

(51) Int. Cl.
*A61B 6/00* (2006.01)
*A61B 90/98* (2016.01)
*A61B 90/00* (2016.01)

(52) U.S. Cl.
CPC ............ *A61B 90/98* (2016.02); *A61B 6/40* (2013.01); *A61B 6/4494* (2013.01); *A61B 6/54* (2013.01);
(Continued)

(58) Field of Classification Search
CPC .... A61B 2090/0803; A61B 2090/0805; A61B 2090/0814; A61B 6/40; A61B 6/4494; A61B 6/54; A61B 6/586; A61B 90/98
See application file for complete search history.

(56) References Cited

U.S. PATENT DOCUMENTS 6,574,518 B1 6/2003 Lounsberry et al.
6,621,890 B1 9/2003 Rondeux
(Continued)

FOREIGN PATENT DOCUMENTS

DE 10057626 A1 5/2001
DE 10057627 A1 5/2001
(Continued)

OTHER PUBLICATIONS

Internation Search Report PCT/ISA/210 for International Application No. PCT/EP2016/068298 dated Aug. 1, 2016.
(Continued)

*Primary Examiner* — Mark R Gaworecki
(74) *Attorney, Agent, or Firm* — Harness, Dickey & Pierce, P.L.C.

(57) ABSTRACT

An X-ray system includes an X-ray source including an electronically readable data carrier on which an identification code is stored; a query device for electronically querying the identification code from the data carrier of the X-ray source; and a disabling device for disabling operation of the X-ray source in the event of the queried identification code deviating from a previously received identification code.

25 Claims, 1 Drawing Sheet

(52) U.S. Cl.
CPC ...... *A61B 6/586* (2013.01); *A61B 2090/0803* (2016.02); *A61B 2090/0805* (2016.02); *A61B 2090/0814* (2016.02)

(56) References Cited

U.S. PATENT DOCUMENTS

| | | |
|---|---|---|
| 7,107,189 B1 | 9/2006 | Lounsberry et al. |
| 2008/0034257 A1 | 2/2008 | Hilderscheid |
| 2009/0080621 A1 | 3/2009 | Flukiger et al. |
| 2011/0013220 A1 | 1/2011 | Sabol et al. |

FOREIGN PATENT DOCUMENTS

| | | |
|---|---|---|
| DE | 69915680 T2 | 3/2005 |
| DE | 102006036832 A1 | 2/2008 |
| DE | 102013206146 A1 | 10/2014 |

OTHER PUBLICATIONS

Written Opinion of the International Search Authority PCT/ISA/237 for International Application No. PCT/EP2016/068298 dated Aug. 1, 2016.

X-RAY SYSTEM COMPRISING AN X-RAY SOURCE

PRIORITY STATEMENT

This application is the national phase under 35 U.S.C. § 371 of PCT International Application No. PCT/EP2016/068298 which has an International filing date of Aug. 1, 2016, which designated the United States of America and which claims priority to German patent application number DE 102015215377.0 filed Aug. 12, 2015, the entire contents of which are hereby incorporated herein by reference.

FIELD

An embodiment of the present invention generally relates to an X-ray system comprising an X-ray source and/or a method for operating an X-ray system.

Different makes of X-ray sources for X-ray units are offered by various manufacturers. The mutual compatibility of the X-ray sources is however is not always guaranteed. If unsuitable X-ray sources from other manufacturers are used in the X-ray unit, malfunctions may occur or the X-ray unit may be damaged.

SUMMARY

At least one embodiment of the invention limits or even prevents the use of unsuitable X-ray sources in an X-ray system.

Advantageous embodiments are set down in the claims, the description and the drawings.

According to a first embodiment, an X-ray system comprises an X-ray source which has an electronically readable data carrier on which an identification code is stored; a query device for electronically querying the identification code from the data carrier of the X-ray source; and a disabling device for disabling operation of the X-ray source in the event of the queried identification code deviating from a predefined identification code. By this embodiment, the technical advantage is achieved that only suitable X-ray sources which can be identified automatically on the basis of the identification code are able to be used in the X-ray system. It is possible to exclude the possibility of endangering staff or damaging the X-ray system as a result of using inappropriate or unsuitable X-ray sources.

According to a second embodiment, an X-ray source includes an electronically readable data carrier on which an identification code for the X-ray source is stored. By this embodiment, the same technical advantages are achieved as by the X-ray system according to the first embodiment.

According to a third embodiment, a method for operating an X-ray system comprises electronically querying an identification code from a data carrier of an X-ray source; and disabling operation of the X-ray source in the event of the queried identification code deviating from a predefined identification code. By this embodiment, the same technical advantages are achieved as by the X-ray system according to the first embodiment.

According to a fourth embodiment, a computer program is stored on an electronically readable data carrier, in a memory or on a non-transitory computer readable medium and includes program code for carrying out the method in accordance with the first embodiment when the computer program is executed on a computer. By this embodiment, the same technical advantages are achieved as by the X-ray system according to the first embodiment.

BRIEF DESCRIPTION OF THE DRAWINGS

Example embodiments of the invention are illustrated in the drawings and will be described in detail in the following.

In the drawings.

DETAILED DESCRIPTION OF THE EXAMPLE EMBODIMENTS

Figure 1:
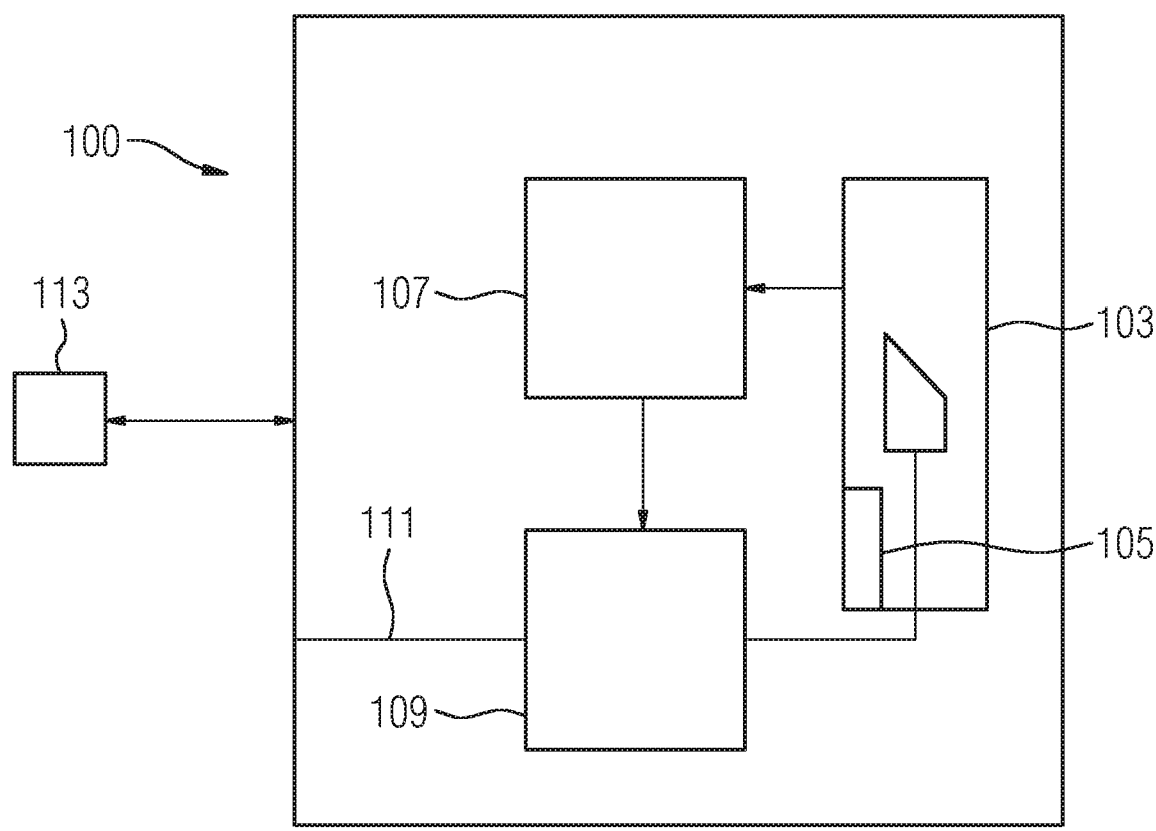
FIG. 1 shows a schematic illustration of an X-ray system of an example embodiment.

According to a first embodiment, an X-ray system comprises an X-ray source which has an electronically readable data carrier on which an identification code is stored; a query device for electronically querying the identification code from the data carrier of the X-ray source; and a disabling device for disabling operation of the X-ray source in the event of the queried identification code deviating from a predefined identification code. By this embodiment, the technical advantage is achieved that only suitable X-ray sources which can be identified automatically on the basis of the identification code are able to be used in the X-ray system. It is possible to exclude the possibility of endangering staff or damaging the X-ray system as a result of using inappropriate or unsuitable X-ray sources.

In an advantageous embodiment of the X-ray system, the data carrier is integrated in the X-ray source. By this embodiment, the technical advantage is achieved for example that the data carrier is an integral element of the X-ray source and can only be exchanged together with the latter.

In a further advantageous embodiment of the X-ray system, the data carrier is a memory chip. By this embodiment, the technical advantage is achieved for example that the identification code can be stored and read in a simple manner.

In a further advantageous embodiment of the X-ray system the identification code is stored in hardwired fashion in the electronically readable data carrier. By this embodiment, the technical advantage is achieved for example that the identification code cannot be modified subsequently.

In a further advantageous embodiment of the X-ray system, the data carrier includes an electronic signature for checking the integrity of the identification code. By this embodiment, the technical advantage is achieved for example that the identification code cannot be falsified.

In a further advantageous embodiment of the X-ray system, the X-ray system includes a receive unit for receiving the predefined identification code from a license server by way of a data network. By this embodiment, the technical advantage is achieved for example that an identification code for enabling the X-ray source can be requested. By this embodiment, it is possible where applicable to use a different make of X-ray source.

In a further advantageous embodiment of the X-ray system, the predefined identification code has a temporally limited validity. By this embodiment, the technical advantage is achieved for example that the X-ray source can only be used in a given period of time.

According to a second embodiment, an X-ray source includes an electronically readable data carrier on which an identification code for the X-ray source is stored. By this embodiment, the same technical advantages are achieved as by the X-ray system according to the first embodiment.

In an advantageous embodiment of the X-ray source, the data carrier is integrated in the X-ray source. By this embodiment, the technical advantage is likewise achieved for example that the data carrier is an integral element of the X-ray source and can only be exchanged together with the latter.

According to a third embodiment, a method for operating an X-ray system comprises electronically querying an identification code from a data carrier of an X-ray source; and disabling operation of the X-ray source in the event of the queried identification code deviating from a predefined identification code. By this embodiment, the same technical advantages are achieved as by the X-ray system according to the first embodiment.

In an advantageous embodiment of the method, the integrity of the queried identification code is checked on the basis of an electronic signature. By this embodiment, the technical advantage is likewise achieved for example that the identification code cannot be falsified.

In a further advantageous embodiment of the method, the predefined identification code is received from a license server by way of a data network. By this embodiment, the technical advantage is likewise achieved for example that a suitable identification code can be requested from the license server.

In a further advantageous embodiment of the method, a notification is sent to the license server when operation of the X-ray source is disabled. By this embodiment, the technical advantage is achieved for example that a central register is kept of when an X-ray source is disabled and servicing of the X-ray system can be performed.

In a further advantageous embodiment of the method, the method is performed prior to setting the operating parameters of the X-ray source in the X-ray system. By this embodiment, the technical advantage is achieved for example that operation of the X-ray source is prevented.

According to a fourth embodiment, a computer program is stored on an electronically readable data carrier, in a memory or on a non-transitory computer readable medium and includes program code for carrying out the method in accordance with the first embodiment when the computer program is executed on a computer. By this embodiment, the same technical advantages are achieved as by the X-ray system according to the first embodiment.

FIG. 1 shows a schematic illustration of an X-ray system 100. The X-ray system 100 is used for examining objects by way of X-rays. The X-rays are emitted by an X-ray source 103 which can be inserted into the X-ray system 100 and can be exchanged. The X-ray source 103 comprises an X-ray tube and a protective housing. After the object has been irradiated the X-rays strike a detector, with the result that an X-ray image of the object is obtained.

The X-ray source 103 additionally comprises an electronically readable data carrier 105 on which is stored an identification code for identifying the X-ray source 103. Furthermore the data carrier 105 can comprise a material number and/or a serial number of the X-ray tube. The data carrier 105 is for example a memory chip on which the identification code is stored in digital form. The storage of the identification code can be affected by way of a hardwired logic circuit which cannot be modified subsequently.

The data carrier 105 is formed for example by way of a ROM memory, an EPROM memory or any other suitable digital memory. The data carrier 105 is assigned to the X-ray source 103, for example enclosed or structurally integrated in the interior of the X-ray source 103.

The identification code can be secured by way of a digital signature of the manufacturer, which means that any falsification of the identification code is recognized. For this purpose a check is made as to whether the digital signature is valid for the identification code. If the digital signature is not valid, an error message can be output and operation of the X-ray source 103 disabled.

A query device 107 is used for electronically querying the identification code from the data carrier 105 of the X-ray source 103. Querying the identification code can take place by way of a control line or a power supply line 111 of the X-ray source 103. The query device 107 is formed for example by an electronic circuit which is capable by way of digital signals of reading the identification code from the X-ray source 103. By this embodiment, the identification code can be read from the data carrier 105, thereby enabling the identification code to be processed further by the X-ray system 100.

The X-ray system 100 furthermore comprises a disabling device 109 for disabling operation of the X-ray source 103 in the event of the queried identification code deviating from a predefined identification code which is obtained through a license. The disabling device 109 is formed for example by an electronic circuit which is capable of preventing the X-ray source 103 from operating. Disabling can take place for example by interrupting a power supply line 111 by way of a relay.

The query device 107 for electronically querying the identification code and the disabling device 109 can moreover be implemented by way of control software or a computer program. The control software or the computer program can be executed by a computer with a memory and a processor which is incorporated in the X-ray system 100. The control software or the computer program can be loaded into the memory of the computer.

The system software recognizes and thus compares the X-ray source 103 using the identification code read (1st code) and the predefined identification code from the license (2nd code) and enables the X-ray system 100 in the event of a match. It can thereby be ensured that the X-ray source 103 is only operated when a valid identification code is present. For this purpose the conventional system software is extended by a corresponding license management for the identification code.

During installation, commissioning and testing of the X-ray system 100 or of the X-ray source 103 the existing X-ray source 103 and the electronically readable data carrier 105 are connected and the configuration of the X-ray source 103 is performed. After the configuration, for example as a result of input of the material number and identification code of the X-ray source, the data is compared and incorporated into the X-ray system 100.

A license for the X-ray source 103 can be requested from a licensing server. For this purpose the identification code, the material number or the serial number of the X-ray source 103 can be specified. When the license has been obtained, the predefined identification code is imported into the X-ray system 100.

Any misuse of the license by specifying the previously used data can be countered by checking the identification code whenever the X-ray source 103 is installed or exchanged. During the installation and subsequent commissioning of a new X-ray source 103 it is necessary to set up (tune up) the operating parameters of the X-ray source 103, for example make settings for current, voltage, time and dose.

The settings function is implemented via an operator interface. Before the settings function is enabled from the operator interface, a query is performed on the identification code of the X-ray source 103 so that the X-ray source 103 is recognized. The system software recognizes the X-ray source 103 on the basis of the queried identification code (1st code) and the predefined identification code from the license (2nd code) and enables the X-ray system 100 in the event of a match. This means that the X-ray system 100 (system software/service software) independently asks for the identification codes from the license and the X-ray source 103 in each case before resetting the operating parameters.

If an X-ray source 103 with an unsuitable identification code is installed, this fact is recognized and the resetting of the operating parameters can be disabled or blocked. In this case a notification can appear to the effect that a member of service staff for the X-ray system 100 should be contacted.

Furthermore, in this case a new special license with a suitable identification code can be requested from a license server, by which the X-ray system 100 is enabled despite the initial non-recognition of the X-ray source 103. For this purpose the X-ray system 100 comprises a receive unit for receiving an identification code from a license server by way of a data network, such as for example the internet. This special license may have a temporally limited validity, for example for a period of three months during which the X-ray source 103 can be exchanged and the operating parameters reset. During this period the X-ray system 100 initially remains enabled, which means that a regular license is only required in the event of subsequent resetting of the operating parameters.

After a certain period of time has elapsed, such as for example 12 months, a renewal of the special license may be required. A notification appears to the effect that a service deployment is required on account of an expired license.

In a first variant embodiment, it is determined that the X-ray source 103 is of a different make from that specified in the configuration and the data of the X-ray source 103 can be registered automatically. In a second variant embodiment, a member of service staff recognizes that the X-ray source 103 is of a different make.

In both cases, a special license can likewise again be provided by a license server 113 in order to enable the X-ray system 100 having a different make of X-ray source 103. In addition, a query for the identification code of the X-ray source 103 can be performed by the license server 113 or service center.

When the special license is granted, a value (flag) is additionally set in the system configuration, which displays a notification to the user in the display when the X-ray system 100 is switched on. The notification relates to the use of a different make of X-ray source 103. The notification can be acknowledged and disappears until the next time the system is switched on again.

If a suitable make is to be installed later, a license query with a new identification code, material number or serial number can be started as described above when commissioning the X-ray system 100.

This ensures that only suitable X-ray sources 103 are inserted into the X-ray system 100 and that the regulations for exchanging the X-ray source 103 are complied with. When exchanging the X-ray source 103 and setting the operating parameters (tune up), special measurements and protocols are carried out, which are stored in a technical folder. As a result of using only suitable X-ray sources 103 the image quality can be maintained after exchanging the X-ray source 103.

A further advantage is the known familiar handling of the licenses and the simple proof of the use or non-use of a suitable make. It is also an advantage that another non-original manufacturer of the X-ray source 103 can obtain a license. A further advantage is that a period of 12 or 24 months of the special license corresponds to an interval of maintenance, so that after the license has expired simultaneous maintenance of the X-ray system 100 can be carried out by member of service staff. The protection with the aid of data carrier and license is applicable to all the components in the X-ray system 100.

Figure 2:
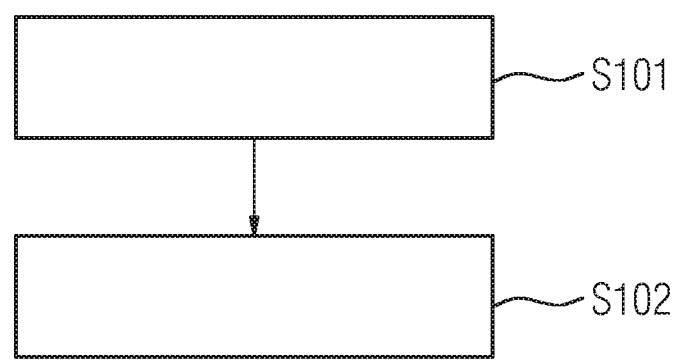
FIG. 2 shows a block diagram of the method of an example embodiment for operating an X-ray system.

FIG. 2 shows a block diagram of the method for operating the X-ray system 100. In a first step S101, the identification code from the data carrier 105 of the X-ray source 103 is electronically queried. In a second step S102, the operation of the X-ray source 103 is disabled in the event of the queried identification code deviating from the predefined identification code.

These steps can be performed each time when the operating parameters are reset or when the X-ray source 103 is exchanged. When operation of the X-ray source 103 is disabled, a notification which specifies the X-ray system 100 can be sent to the license server 113 over the internet. In this case a member of service staff can be assigned to perform maintenance.

All the features explained and shown in connection with individual embodiments of the invention can be provided in various combinations in the subject matter according to the invention in order to simultaneously implement their advantageous effects. Features which have been described in relation to method steps can be implemented by way of corresponding object features which are designed in order to execute the respective method steps, and vice versa.

The scope of protection of the embodiments of the present invention is given by the claims and is not limited by the features explained in the description or shown in the figures.

The invention claimed is:

1. An X-ray system, comprising:
   an X-ray source including an electronically readable data carrier storing a first identification code, the first identification code uniquely identifying the X-ray source;
   a query device to electronically query the first identification code from the electronically readable data carrier of the X-ray source;
   a disabling device to disable operation of the X-ray source in response to the electronic query indicating that the first identification code deviates from a second identification code received from a license server; and
   a receiver to receive the second identification code from the license server via a data network.

2. The X-ray system of claim 1, wherein the electronically readable data carrier is integrated in the X-ray source.

3. The X-ray system of claim 2, wherein the electronically readable data carrier is a memory chip.

4. The X-ray system of claim 2, wherein the first identification code is stored in hardwired fashion in the electronically readable data carrier.

5. The X-ray system of claim 2, wherein the electronically readable data carrier includes an electronic signature for checking integrity of the first identification code.

6. The X-ray system of claim 2, wherein the second identification code has a temporally limited validity.

7. The X-ray system of claim 1, wherein the electronically readable data carrier is a memory chip.

8. The X-ray system of claim 7, wherein the first identification code is stored in hardwired fashion in the electronically readable data carrier.

9. The X-ray system of claim 7, wherein the electronically readable data carrier includes an electronic signature for checking integrity of the first identification code.

10. The X-ray system of claim 7, wherein the second identification code has a temporally limited validity.

11. The X-ray system of claim 1, wherein the first identification code is stored in hardwired fashion in the electronically readable data carrier.

12. The X-ray system of claim 1, wherein the electronically readable data carrier includes an electronic signature for checking integrity of the first identification code.

13. The X-ray system of claim 1, wherein the second identification code has a temporally limited validity.

14. An X-ray source, comprising:
   an electronically readable data carrier storing an identification code uniquely identifying the X-ray source.

15. The X-ray source of claim 14, wherein the electronically readable data carrier is integrated in the X-ray source.

16. The X-ray source of claim 14, wherein the electronically readable data carrier is a memory chip.

17. A method for operating an X-ray system, the method comprising:
   electronically querying first identification code from a data carrier of an X-ray source of the X-ray system, the first identification code uniquely identifying the X-ray source; and
   disabling operation of the X-ray source in response to the electronically querying indicating that the first identification code deviates from a second identification code received from a license server via a data network.

18. The method of claim 17, further comprising:
   checking integrity of the first identification code based on an electronic signature.

19. The method of claim 18, further comprising:
   sending a notification to the license server in response to disabling the operation of the X-ray source.

20. The method of claim 18, wherein the method is performed prior to setting operating parameters of the X-ray source in the X-ray system.

21. The method of claim 17, further comprising:
   sending a notification to the license server in response to disabling the operation of the X-ray source.

22. The method of claim 21, wherein the method is performed prior to setting operating parameters of the X-ray source in the X-ray system.

23. The method of claim 17, wherein the method is performed prior to setting operating parameters of the X-ray source in the X-ray system.

24. A non-transitory computer readable medium including a computer program with program code for carrying out the method of claim 17 when the computer program is executed on a computer.

25. The non-transitory computer readable medium of claim 24, wherein the non-transitory computer readable medium is a memory.

* * * * *